(12) United States Patent
Toyoshima et al.

(10) Patent No.: US 10,398,638 B2
(45) Date of Patent: Sep. 3, 2019

(54) POWDER DISPERSANT, AND POWDER DISPERSION COMPOSITION AND COSMETIC PRODUCT CONTAINING THE SAME

(71) Applicant: SAKAMOTO YAKUHIN KOGYO CO., LTD., Osaka-shi, Osaka (JP)

(72) Inventors: Ryosuke Toyoshima, Izumi (JP); Takeshi Yamada, Izumi (JP)

(73) Assignee: SAKAMOTO YAKUHIN KOGYO CO., LTD., Osaka-Shi, Osaka (JP)

( * ) Notice: Subject to any disclaimer, the term of this patent is extended or adjusted under 35 U.S.C. 154(b) by 0 days.

(21) Appl. No.: 15/492,047

(22) Filed: Apr. 20, 2017

(65) Prior Publication Data

US 2017/0216187 A1  Aug. 3, 2017

Related U.S. Application Data

(63) Continuation of application No. PCT/JP2015/081801, filed on Nov. 12, 2015.

(30) Foreign Application Priority Data

Nov. 17, 2014  (JP) ................................ 2014-233160

(51) Int. Cl.

| | |
|---|---|
| A61K 8/04 | (2006.01) |
| A61K 8/06 | (2006.01) |
| A61Q 17/04 | (2006.01) |
| A61Q 19/00 | (2006.01) |
| C11C 3/00 | (2006.01) |
| A61K 8/85 | (2006.01) |
| C09D 17/00 | (2006.01) |
| A61Q 1/12 | (2006.01) |
| A23D 9/00 | (2006.01) |
| C09D 5/03 | (2006.01) |
| A61K 8/39 | (2006.01) |
| A61Q 1/02 | (2006.01) |

(52) U.S. Cl.
CPC .................. *A61K 8/85* (2013.01); *A23D 9/00* (2013.01); *A61K 8/04* (2013.01); *A61K 8/062* (2013.01); *A61K 8/064* (2013.01); *A61K 8/39* (2013.01); *A61Q 1/02* (2013.01); *A61Q 1/12* (2013.01); *A61Q 17/04* (2013.01); *C09D 5/03* (2013.01); *C09D 17/00* (2013.01); *C11C 3/003* (2013.01); *A61K 2800/262* (2013.01)

(58) Field of Classification Search
None
See application file for complete search history.

(56) References Cited

U.S. PATENT DOCUMENTS

| | | | |
|---|---|---|---|
| 2006/0165627 A1* | 7/2006 | Allef | .................. A61K 8/39 424/70.11 |
| 2007/0269470 A1 | 11/2007 | Takeda et al. | |
| 2013/0237672 A1* | 9/2013 | Rouse | ................... A61K 8/361 525/437 |
| 2013/0281552 A1* | 10/2013 | Nilewski | ........... B01D 19/0404 516/133 |

FOREIGN PATENT DOCUMENTS

| | | |
|---|---|---|
| EP | 1857091 A1 | 11/2007 |
| EP | 2374787 A1 | 10/2011 |
| JP | S59-27807 A | 2/1984 |
| JP | S60-87206 A | 5/1985 |
| JP | H06-39272 A | 2/1994 |
| JP | H08-003026 A | 1/1996 |
| JP | 2001-58926 A | 3/2001 |
| JP | 2004-169015 A | 6/2004 |
| JP | 2005-89487 A | 4/2005 |
| JP | 2007-161648 A | 6/2007 |
| JP | 2007-197332 A | 8/2007 |
| JP | 2008-239550 A | 10/2008 |
| JP | 2012-184178 A | 9/2012 |
| WO | WO-2006/095486 A1 | 9/2006 |
| WO | WO-2010/070808 A1 | 6/2010 |

* cited by examiner

*Primary Examiner* — Ernst V Arnold
*Assistant Examiner* — Kyung S Chang
(74) *Attorney, Agent, or Firm* — Rabin & Berdo, P.C.

(57) ABSTRACT

A powder dispersant includes an ester compound of a polyglycerol having an average degree of polymerization of the polyglycerol, calculated from its hydroxyl value, in the range 2 to 20, a monovalent carboxylic acid or at least one derivative thereof, and a divalent carboxylic acid or at least one derivative thereof.

9 Claims, No Drawings

POWDER DISPERSANT, AND POWDER DISPERSION COMPOSITION AND COSMETIC PRODUCT CONTAINING THE SAME

CROSS-REFERENCE TO RELATED APPLICATIONS

This application is a continuation application under 35 U.S.C. 120 of International Application PCT/JP2015/081801 having the International Filing Date of Nov. 12, 2015, and claims the priority of Japanese Patent Application No. 2014-233160, filed on Nov. 17, 2014. The identified applications are fully incorporated herein by reference.

BACKGROUND OF THE INVENTION

Technical Field

The present invention relates to a powder dispersant, and a powder dispersion composition and a cosmetic product containing the powder dispersant.

Background Art

Powders contained in various products such as cosmetic products and industrial materials, while exerting various functions, have high aggregation properties and therefore it is necessary to maintain uniform dispersion in such a product and stability over time, for which various dispersants have been studied. Of the cosmetic products, sunscreen cosmetics and the like having a UV protection function contain a powder as a UV absorbing scattering agent, where a micronized powder having a particle size of 10 to 500 nm is used for purposes such as increasing the UV absorption capacity of the powder and preventing the powdery finish when applied to the skin so as to improve the transparency (see Japanese Patent Laid-Open No. 08-3026, hereinafter referred to as Patent Literature (PL) 1). Further, in order to improve the UV protection function and the transparency, it is necessary to uniformly disperse the powder, for which a powder dispersant is contained therein. As a powder dispersant, ricinoleic acid and hydroxystearic acid (see Japanese Patent Laid-Open No. 06-39272, hereinafter referred to as PL2), polyhydroxystearic acid (see Japanese Patent Laid-Open No. 2012-184178, hereinafter referred to as PL3), siliconized polyglycerol (polyglycerin) (see Japanese Patent Laid-Open No. 2007-161648, hereinafter referred to as PL4), polyether modified silicone (see Japanese Patent Laid-Open No. 2001-58926, hereinafter referred to as PL5), polyglycerol modified silicone (see Japanese Patent Laid-Open No. 2004-169015, hereinafter referred to as PL6), and the like are used. The micronized powder as in PL1 is difficult to disperse because of its large surface area and a high aggregation force, and the dispersion is more difficult particularly in the case where there is a significant difference in polarity among oil agents, as in the cosmetic products. The case of using an organic UV absorber that is a compound with a high polarity and a non-polar oil agent such as silicone oil applies to the above case. In the case of using ricinoleic acid, hydroxystearic acid, or polyhydroxystearic acid as a dispersant, as in PLs2 and 3, in such oil agents, a large amount of the dispersant needs to be contained therein, where it is sticky in use, and further its stability over time is also insufficient. The silicone dispersants used in PLs4, 5, and 6 are low HLB surfactants in which a hydrophilic moiety is introduced into a silicone chain and silicone serves as a backbone, and therefore, with such dispersants, dispersion is easily maintained in a silicone oil, while a powder tends to aggregate in an organic UV absorber with a high polarity. Further, in oil-in-water (O/W) emulsified cosmetic products and water-in-oil (W/O) emulsified cosmetic products which contain water, the powder dispersibility may sometimes decrease due to the orientation of the dispersant at the interface between oil and water. Further, these dispersants have a high molecular weight, and therefore there are problems in usability such as the occurrence of stickiness.

SUMMARY OF THE INVENTION

An object is to provide a powder dispersant having excellent dispersibility and usability with good spreadability without stickiness, and a powder dispersion composition and a cosmetic product containing the powder dispersant.

As a result of diligent studies in order to solve the above problems, the inventors have found that a dispersant using a specific polyglycerol (polyglycerine or polyglycerin) fatty acid ester can solve the aforementioned problems, so as to accomplish the invention. That is, the invention relates to a powder dispersant comprising an ester compound of a polyglycerol having an average degree of polymerization of the polyglycerol, calculated from its hydroxyl value, in the range, 2 to 20, at least one monovalent carboxylic acid, and a divalent carboxylic acid or at least one derivative thereof.

The invention also relates to a powder dispersion composition and a cosmetic product containing the aforementioned powder dispersant.

The invention can provide a powder dispersion composition and a cosmetic product containing the powder dispersant with improved dispersibility in an oil agent composition having a wide range of polarity, improved stability over time, and improved usability without stickiness.

DETAILED DESCRIPTION FOR THE INVENTION

Hereinafter, an exemplary embodiment of the invention will be described in detail.

A powder dispersant of the exemplary embodiment can use an ester compound of a polyglycerol having an average degree of polymerization of the polyglycerol, calculated from its hydroxyl value, in the range 2 to 20, a monovalent carboxylic acid or at least one derivative thereof, and a divalent carboxylic acid or at least one derivative thereof.

The polyglycerol used in the exemplary embodiment is not particularly limited as long as it is a polyglycerol having an average polymerization degree of the polyglycerol, calculated from its hydroxyl value, of 2 to 20. Examples of such a polyglycerol include diglycerol, triglycerol, tetraglycerol, pentaglycerol, hexaglycerol, heptaglycerol, octaglycerol, nonaglycerol, decaglycerol, hexadecaglycerol, octadecaglycerol, and eicosaglycerol, in which tetraglycerol, pentaglycerol, hexaglycerol, heptaglycerol, octaglycerol, nonaglycerol, and decaglycerol are particularly preferable in view of the effects of the present invention.

The monovalent carboxylic acid used in the exemplary embodiment is not particularly limited. Examples of the monovalent carboxylic acid include acetic acid, propionic acid, butyric acid, valeric acid, caproic acid, caprylic acid, 2-ethylhexanoic acid, isononanoic acid, capric acid, lauric acid, myristic acid, isomyristic acid, palmitic acid, isopalmitic acid, stearic acid, isostearic acid, ricinoleic acid, oleic acid, linoleic acid, linolenic acid, arachidic acid, isoarachidic acid, behenic acid, and erucic acid. Further, acid anhydrides or acid halides thereof may be used.

The divalent carboxylic acid used in the exemplary embodiment is not particularly limited. Examples of the divalent carboxylic acid include carboxylic acids such as oxalic acid, malonic acid, succinic acid, glutaric acid, adipic acid, pimelic acid, suberic acid, azelaic acid, sebacic acid, dimethyloctadecanedioic acid, eicosanedioic acid, phthalic acid, isophthalic acid, terephthalic acid, maleic acid, dimer acid, tetrahydrophthalic acid, octenylsuccinic acid, and dodecenylsuccinic acid. Further, acid anhydrides or acid halides thereof may be used.

The rate of esterification of the polyglycerol ester of the exemplary embodiment is not particularly limited, and the rate of esterification is particularly preferably 75% to 100%, in view of the effects of the present invention.

The mixing molar ratio of the monovalent carboxylic acid to the divalent carboxylic acid is not particularly limited, and the mixing molar ratio of the monovalent carboxylic acid to the divalent carboxylic acid is preferably 99.99/0.01 to 0.01/99.99, further preferably 95.0/5.0 to 50/50, in view of the effects of the present invention.

As a method for producing the powder dispersant of the exemplary embodiment, a commonly used esterification reaction can be used. For example, the esterification reaction can be performed using paratoluenesulfonic acid, sulfuric acid, hydrochloric acid, methanesulfonic acid, boron trifluoride-diethyl ether complex, sodium hydroxide, potassium hydroxide, or the like, as a catalyst, and using heptane, hexane, cyclohexane, toluene, xylene, or the like, as a solvent. Alternatively, the esterification can be performed in the absence of a solvent or in the absence of a catalyst. The obtained ester can be used as it is or can be used after being purified by a common method, as needed.

The powder used in the powder dispersion composition of the exemplary embodiment is not specifically limited in terms of a shape such as a spherical shape, a plate shape, and an acicular shape, a particle size such as a fume particle size, a fine particle size, and a pigment particle size, or a particle structure such as a porous particle structure and a non-porous particle structure, and examples thereof include inorganic powders, luminescent powders, organic powders, dye powders, metal powders, and composite powders. That is, examples of the powder used in the powder dispersion composition of the exemplary embodiment include white inorganic pigments such as titanium oxide, zinc oxide, cerium oxide, and barium sulfate, colored inorganic pigments such as iron oxide, ultramarine blue, iron blue ($CoO \cdot Al_2O_3 \cdot SiO_2$ or $Fe_4[Fe(CN)_6]_3$), carbon black, titanium-titanium oxide sintered materials, chromium oxide, and chromium hydroxide, white extender powders such as talc, white mica, gold mica, red mica, black mica, synthetic mica, silk mica, synthetic sericite, silicon carbide, silicon dioxide, aluminum oxide, magnesium oxide, zirconium oxide, antimony oxide, diatomite, aluminum silicate, aluminum magnesium metasilicate, calcium silicate, barium silicate, magnesium silicate, calcium carbonate, magnesium carbonate, hydroxyapatite, and boron nitride, clay minerals such as kaolin, bentonite, smectite, hectorite, and montmorillonite and organically modified products thereof, luminescent powders such as titanium oxide coated mica, titanium oxide coated bismuth oxychloride, iron oxide mica titanium, iron blue treated mica titanium, carmine treated mica titanium, bismuth oxychloride, fish scales, polyethylene terephthalate-aluminum-epoxy laminated films, polyethylene terephthalate-polyolefin laminated films, and titanium oxide coated glass flakes, copolymer resins such as polyamide resins, polyethylene resins, polyacrylic resins, polyester resins, fluorine resins, cellulose resins, polystyrene resins, and styrene-acrylic copolymer resins, organic polymer resin powders such as polypropylene resins, silicone resins, and urethane resins, organic low-molecular weight powders such as zinc stearate and N-acyllysine, natural organic powders such as silk powder and cellulose powder, organic pigment powders such as red No. 201, red No. 202, red No. 205, red No. 226, red No. 228, orange No. 203, orange No. 204, blue No. 404, and yellow No. 401, organic pigment powders of zirconium, barium, aluminum rake, or the like, such as red No. 3, red No. 104, red No. 106, orange No. 204, yellow No. 4, yellow No. 5, green No. 3, and blue No. 1, and metal powders such as aluminum powder, gold powder, and silver powder. Further, complex of these may be used. These powders may be applied to a surface treatment using one or two or more of fluorine compounds, silicone compounds, metal soaps, lecithin, hydrogenated lecithin, collagen, hydrocarbons, higher fatty acids, higher alcohols, esters, waxes, and surfactants.

Further, liquid oils are used as the oil agents used in the powder dispersion composition of the exemplary embodiment, and examples thereof include hydrocarbons such as liquid paraffin, liquid isoparaffin, squalane, pristane, α-olefin oligomer, and polyethylene, plant fats and oils such as avocado oil, linseed oil, almond oil, olive oil, cacao butter, carrot oil, cucumber oil, candlenut oil, grape seed oil, sesame oil, wheat germ oil, rice bran oil, safflower oil, soybean oil, tea oil, evening primrose oil, camellia oil, corn oil, rapeseed oil, persic oil, coix seed oil, palm oil, palm kernel oil, castor oil, sunflower oil, hazelnut oil, macadamia nut oil, meadowfoam oil, cottonseed oil, peanut oil, rose hip oil, sasanqua oil, jojoba oil, clove oil, lavender oil, rosemary oil, turpentine oil, and eucalyptus oil, animal oils such as orange ruffy oil, ester oils such as avocado oil fatty acid ethyl, dioctyl adipate, diisopropyl adipate, diisobutyl adipate, di-2-hexyldecyl adipate, diheptyl undecyl adipate, alkyl benzoate (C12-15), isostearyl glyceryl, hexyldecyl isostearate, isopropyl isostearate, octyldodecyl isostearate, isocetyl isostearate, isostearyl isostearate, glyceryl isostearate, batyl isostearate, alkyl octanoate (C12-15), ethylene glycol fatty acid ester, octyldodecyl erucate, pentaerythritol octanoate, cetyl octanoate, isocetyl octanoate, cetearyl octanoate, isostearyl octanoate, ethyl oleate, oleyl oleate, ethylene glycol dioleate, glyceryl trioleate, octyldodecyl oleate, decyl oleate, glyceryl tricaprylate, cetyl ethylhexanoate, octyldodecyl erucate, cetostearyl ethylhexanoate, propylene glycol dicaprylate, neopentyl glycol dicaprate, neopentyl glycol dioctanoate, ethylene glycol dioctanoate, propylene glycol dicaprate, hexyldecyl neodecanoate, hexyldecyl stearate, isocetyl stearate, butyl stearate, cetyl isooctanate, diisopropyl sebacate, diethyl sebacate, diisopropyl dimerate, dialkyl carbonate (C14,15), pentaerythrityl isostearate, pentaerythrityl tetraoctanoate, glyceryl triisostearate, diglyceryl diisostearate, glyceryl trioctanoate, diglyceryl triisostearate, diglyceryl tetraisostearate, decaglyceryl pentaisostearate, decaglyceryl nonaisostearate, decaglyceryl decaisostearate, trimethylolpropane triisostearate, trioctanoin, trimethylolpropane trioctanoate, hexyldecyl dimethyl octanoate, octyldodecyl dimethyl octanoate, isononyl isononanoate, isodecyl isononanoate, tridecyl isononanoate, isotridecyl isononanoate, propylene glycol dinonanoate, octyl nonanoate, octyl isononanoate, glyceryl tri(caprylate/caprate), glyceryl trimyristate, cetyl lactate, myristyl lactate, lauryl lactate, octyldodecyl lactate, isostearyl palmitate, isopropyl palmitate, octyl palmitate, cetyl palmitate, isocetyl palmitate, octyl isopalmitate, 2-ethylhexyl hydroxystearate, isotridecyl myristate, isocetyl myristate, isostearyl myristate, isopropyl myristate, octyldodecyl myristate, hexyl laurate, isostearyl laurate, tocopherol linoleate, octyldodecyl ricinoleate, diisostearyl malate, polypropylene glycol succinate oligoester, and di-2-ethylhexyl succinate, dimethyl polysiloxane with a low degree of polymerization, dimethyl polysiloxane with a high degree of polymerization, methylphenylpolysiloxane, methylhydrogenpolysiloxane, octamethylcyclotetrasiloxane, decamethylcyclopentasiloxane, dodecamethylcyclohexasiloxane, alkyl modified polysiloxane, amino modified polysiloxane, crosslinked organopolysiloxane, and fluorine modified polysiloxane.

Further, the method for obtaining the powder dispersion composition of the exemplary embodiment is not specifically limited, but the powder dispersion composition of the exemplary embodiment can be easily obtained, for example, by a method comprising dissolving or dispersing the powder dispersant of the exemplary embodiment in the aforementioned oil agents, adding a powder, and mixing them using a disperser such as a ball mill, a bead mill, and a sand mill.

Further, the dosage form or product form of the cosmetic product of the exemplary embodiment prepared by adding the powder dispersant or the powder dispersion composition of the exemplary embodiment is not specifically limited. The cosmetic product of the exemplary embodiment can be applied in various forms such as a water-in-oil type form, oil-in-water type form, oily type form, water dispersion type form, and powder type form. Furthermore, the cosmetic product of the exemplary embodiment can be various products such as skin cosmetics and finishing cosmetics. Examples of the skin cosmetics may be facial foam/cream, cleansing, massage cream, pack, lotion, milky lotion, cream, serum, makeup base, and sunscreen, and examples of finishing cosmetics may be foundation, white powder, eye shadow, eyeliner, mascara, eyebrow, concealer, lipstick, lip gloss, and lip balm. Furthermore, sunscreen, foundation, makeup base, and the like can preferably be used since such cosmetic product of the exemplary embodiment may have greater effects.

Further, the powder dispersant or the powder dispersion composition of the exemplary embodiment can be used for pharmaceutical products, paints, inks, optical filters, and the like, other than the cosmetic applications.

Moreover, the cosmetic product of the exemplary embodiment can contain additional compounds such as compounds that are generally contained in cosmetic products and compounds other than the powders used in the powder dispersion compositions and the oil agents as explained above, as long as the effects of the present invention are not degraded.

That is, examples of the compounds that can be contained in the cosmetic product containing the powder dispersant of the exemplary embodiment include waxes such as solid paraffin, ceresin, ozokerite, ethylene-propylene copolymer, polyethylene wax, Fischer-Tropsch wax, candelilla wax, microcrystalline wax, and jojoba wax, waxes such as beeswax, carnauba wax, lanolin wax, rice bran wax, insect wax, and Japan wax, fatty acids such as arachidonic acid, isostearic acid, undecylenic acid, erucic acid, oleic acid, stearic acid, sebacic acid, palmitic acid, behenic acid, myristic acid, lauric acid, lanolin fatty acid, linoleic acid, linolenic acid, capric acid, caprylic acid, hydroxystearic acid, safflower oil fatty acid, rice bran fatty acid, tall oil fatty acid, and coconut fatty acid, higher alcohols such as isostearyl alcohol, oleyl alcohol, octyl dodecanol, octyl alcohol, decyl alcohol, arachyl alcohol, hexyl decanol, chimyl alcohol, β-glucan, cholesterol, sitosterol, dihydrocholesterol, stearyl alcohol, cetanol, cetostearyl alcohol, phytosterol, hexyl decanol, behenyl alcohol, lauryl alcohol, lanolin alcohol, and myristyl alcohol, polyhydric alcohols such as erythritol, glycerol, xylitol, diglycerol, dipropylene glycol, sorbit, trehalose, 1,3-butylene glycol, propylene glycol, 1,2-pentanediol, polyethylene glycol, polyoxyethylene glycerol, polypropylene, polyoxypropylene glyceryl ether, polyoxypropylene diglyceryl ether, polyoxypropylene butyl ether, polyoxyethylene-polyoxypropylene butyl ether, polyoxyethylene methyl glucoside, polyglycerol, maltitol, and mannitol, mucopolysaccharides such as sodium hyaluronate, sodium acetyl hyaluronate, and sodium chondroitin sulfate, thickening/film forming agents such as arabic gum, carboxyvinyl polymer, sodium alginate, propylene glycol alginate, ethyl cellulose, guar hydroxypropyl trimonium chloride, carrageenan, karaya gum, sodium carboxymethylcellulose, agar, xanthan gum, guar gum, quince seed gum, synthetic sodium silicate-magnesium, (vinylpyrrolidone/VA) copolymer, gellan gum, cyclodextrin, dimethyl distearyl ammonium hectorite, cellulose derivatives, tamarind gum, dextrin fatty acid ester, starches, sodium starch phosphate, tragacanth gum, hydroxyethyl cellulose, pectin, polyacrylic acid amide, sodium polyacrylate, polyvinyl alcohol, polyvinylpyrrolidone, methyl cellulose, locust bean gum, pentaerythritol rosinate, hydroxypropylmethylcellulose, vinyl acetate-vinylpyrrolidone copolymer, vinyl acetate-crotonic acid copolymer, vinyl methyl ether-butyl maleate copolymer, crotonic acid-vinyl acetate-vinyl neodecanoate copolymer, vinylpyrrolidone-styrene copolymer, alkyl acrylate copolymer, polyacrylic acid, sodium polyacrylate, alkyl polyacrylate, acrylic acid amide-styrene copolymer, acrylic acid-acrylic acid amide-ethyl acrylate copolymer, octylamide acrylate-hydroxypropyl acrylate-butyl aminoethyl methacrylate copolymer, acrylic resin-alkanol amine solution, hydroxyethyl acrylate-methoxyethyl acrylate copolymer, cationized cellulose, cationized guar gum, and methacryloyl ethyl dimethyl dimethyl betaine-methacryloyl ethyl trimethyl ammonium chloride-methoxypolyethylene glycol methacrylate copolymer, silicone oils such as methyl polysiloxane, dimethyl polysiloxane, methylphenyl polysiloxane, and cyclic silicone oil, silicone film forming agents such as trimethylsiloxysilicate and crosslinked methylpolysiloxane, silicone derivatives such as aminopropyl dimethicone, alkyl methicone, (dimethicone/vinyl dimethicone) crosspolymer, (stearoxymethicone/dimethicone) copolymer, (dimethylsiloxane/methylcetyloxysiloxane) copolymer, dimethicone, stearyl dimethicone, cetyl dimethicone copolymer, methyl hydrogen polysiloxane, diphenyl dimethicone, phenyl trimethicone, polyether modified organopolysiloxane, polyoxyalkylene alkyl methyl polysiloxane-methyl polysiloxane copolymer, and alkoxy modified polysiloxane, fluorine oils such as fluorine modified organopolysiloxane, perfluorodecane, perfluorooctane, and perfluoropolyether, oily gelling agents such as dextrin fatty acid ester, sucrose fatty acid ester, starch fatty acid ester, 12-hydroxystearic acid, aluminum isostearate, and calcium stearate, anionic surfactants such as alkyl sulfate, polyoxyethylene alkyl ether sulfate, N-acylamino acid salts, alkyl ether carboxylate, fatty acid soaps, alkyl phosphate, polyoxyethylene alkyl ether phosphate, and N-acyl taurine salt, amphoteric surfactants such as betaine acetate amphoteric surfactant, imidazoline amphoteric surfactant, alkylamidopropylbetaine amphoteric surfactant, alkylhydroxysulfobetaine amphoteric surfactant, alkylcarboxymethylhydroxyethyl imidazolinium betaine amphoteric surfactant, and alkyldimethylamine oxide, nonionic surfactants such as propylene glycol fatty acid ester, glycerol fatty acid ester, polyglycerol fatty acid ester, polyoxyethylene glycerol fatty acid ester, sucrose fatty acid ester, sorbitan fatty acid ester, polyoxyethylene sorbitan fatty acid ester, polyoxyethylene sorbitol fatty acid ester, polyoxyethylene lanolin, polyoxyethylene lanolin alcohol, polyoxyethylene sorbitol beeswax, polyoxyethylene castor oil, polyoxyethylene hardened castor oil, polyoxyethylene sterol, polyoxyethylene hydrogenated sterol, polyoxyethylene alkyl ether, polyoxyethylene polyoxypropylene alkyl ether, polyethylene glycol fatty acid ester, alkyl glyceryl ether, alkyl polyglycoside, and alkyl alkanol amide, cationic surfactants such as alkyl ammonium salt and amidoamine, and lecithin derivatives such as hydrogenated soybean phospholipid and hydroxylated soybean phospholipid.

Further, the examples include alcohols such as ethanol and isopropyl alcohol, chelating agents such as edetate, hydroxyethanediphosphonate, polyphosphate, and gluconic acid, preservatives such as benzoate, photosensitizer, parabens, phenoxyethanol, salicylic acid, sorbic acid, and isopropylmethylphenol, whitening agents such as arbutin, ellagic acid, kojic acid, and ascorbate derivatives, vitamins, UV absorbers, amino acids, glycyrrhizic acid derivatives, plant extracts, perfumes, essential oils, and pH adjusters.

EXAMPLES

Hereinafter, the exemplary embodiment will be described more specifically by way of examples and comparative examples, but the scope of the exemplary embodiment is not limited at all by these examples.

Powder Dispersant

Example 1

92.8 g (0.559 mol) of diglycerol and 409.7 g (1.443 mol) of isostearic acid were put into a reaction chamber, and 0.25 g of sodium hydroxide was added thereto, for performing a reaction under a nitrogen stream at 240° C. for 4 hours, and 477 g of an initial esterification reaction product was obtained. 477 g of the aforementioned ester and 27.7 g (0.235 mol) of succinic acid were put in a chamber for performing a reaction under a nitrogen stream at 100° C. for 3 hours, and 500 g of a reaction product having a rate of esterification of 75% was obtained by this two-stage esterification reaction.

Example 2

99.1 g (0.413 mol) of triglycerol and 403.4 g (1.420 mol) of isostearic acid were put into a reaction container, and 0.25 g of sodium hydroxide was added thereto, for performing a reaction under a nitrogen stream at 240° C. for 5 hours, and 477 g of an esterification reaction product was obtained. 477 g of the aforementioned ester and 27.3 g (0.231 mol) of succinic acid were put in a chamber for performing a reaction under a nitrogen stream at 100° C. for 3 hours, and 500 g of a reaction product having a rate of esterification of 80% was obtained.

Example 3

100.5 g (0.320 mol) of tetraglycerol and 401.9 g (1.415 mol) of isostearic acid were put into a reaction container, and 0.25 g of sodium hydroxide was added thereto, for performing a reaction under a nitrogen stream at 240° C. for 6 hours, and 477 g of an esterification reaction product was obtained. 477 g of the aforementioned ester and 27.2 g (0.231 mol) of succinic acid were put in a chamber for performing a reaction under a nitrogen stream at 100° C. for 3 hours, and 500 g of a reaction product having a rate of esterification of 86% was obtained.

Example 4

107.0 g (0.232 mol) of hexaglycerol and 394.8 g (1.390 mol) of isostearic acid were put into a reaction container, and 0.25 g of sodium hydroxide was added thereto, for performing a reaction under a nitrogen stream at 240° C. for 7 hours, and 477 g of an esterification reaction product was obtained. 477 g of the aforementioned ester and 27.3 g (0.232 mol) of succinic acid were put in a chamber for performing a reaction under a nitrogen stream at 100° C. for 3 hours, and 500 g of a reaction product having a rate of esterification of 88% was obtained.

Example 5

110.1 g (0.145 mol) of decaglycerol and 390.2 g (1.374 mol) of isostearic acid were put into a reaction container, and 0.25 g of sodium hydroxide was added thereto, for performing a reaction under a nitrogen stream at 240° C. for 8 hours, and 476 g of an esterification reaction product was obtained. 476 g of the aforementioned ester and 28.8 g (0.244 mol) of succinic acid were put in a chamber for performing a reaction under a nitrogen stream at 100° C. for 3 hours, and 500 g of a reaction product having a rate of esterification of 92% was obtained.

Example 6

132.5 g (0.287 mol) of hexaglycerol and 285.1 g (1.004 mol) of isostearic acid were put into a reaction container, and 0.25 g of sodium hydroxide was added thereto, for performing a reaction under a nitrogen stream at 240° C. for 7 hours, and 400 g of an esterification reaction product was obtained. 400 g of the aforementioned ester and 118.5 g (1.004 mol) of succinic acid were put in a chamber for performing a reaction under a nitrogen stream at 100° C. for 3 hours, and 500 g of a reaction product having a rate of esterification of 88% was obtained.

Example 7

113.1 g (0.245 mol) of hexaglycerol and 367.1 g (1.293 mol) of isostearic acid were put into a reaction container, and 0.25 g of sodium hydroxide was added thereto for performing a reaction under a nitrogen stream at 240° C. for 7 hours, and 457 g of an esterification reaction product was obtained. 457 g of the aforementioned ester and 50.8 g (0.431 mol) of succinic acid were put in a chamber for performing a reaction under a nitrogen stream at 100° C. for 3 hours, and 500 g of a reaction product having a rate of esterification of 88% was obtained.

Example 8

101.8 g (0.220 mol) of hexaglycerol and 417.3 g (1.469 mol) of isostearic acid were put into a reaction container, and 0.25 g of sodium hydroxide was added thereto, for performing a reaction under a nitrogen stream at 240° C. for 8 hours, and 493 g of an esterification reaction product was obtained. 493 g of the aforementioned ester and 8.8 g (0.074 mol) of succinic acid were put in a chamber, for performing a reaction under a nitrogen stream at 100° C. for 3 hours, and 500 g of a reaction product having a rate of esterification of 88% was obtained.

Example 9

175.3 g (0.379 mol) of hexaglycerol and 327.8 g (2.276 mol) of caprylic acid were put into a reaction container, and 0.25 g of sodium hydroxide was added thereto, for performing a reaction under a nitrogen stream at 240° C. for 7 hours, and 462 g of an esterification reaction product was obtained. 462 g of the aforementioned ester and 44.8 g (0.379 mol) of succinic acid were put in a chamber for performing a reaction under a nitrogen stream at 100° C. for 3 hours, and 500 g of a reaction product having a rate of esterification of 88% was obtained.

Example 10

175.3 g (0.379 mol) of hexaglycerol and 327.8 g (2.276 mol) of 2-ethylhexanoic acid were put into a reaction container, and 0.25 g of sodium hydroxide was added thereto, for performing a reaction under a nitrogen stream at 240° C. for 7 hours, and 462 g of an esterification reaction product was obtained. 462 g of the aforementioned ester and 44.8 g (0.379 mol) of succinic acid were put in a chamber for performing a reaction under a nitrogen stream at 100° C. for 3 hours, and 500 g of a reaction product having a rate of esterification of 88% was obtained.

Example 11

139.7 g (0.302 mol) of hexaglycerol and 362.8 g (1.814 mol) of lauric acid were put into a reaction container, and 0.25 g of sodium hydroxide was added thereto, for performing a reaction under a nitrogen stream at 240° C. for 7 hours, and 470 g of an esterification reaction was obtained product. 470 g of the aforementioned ester and 35.7 g (0.302 mol) of succinic acid were put in a chamber for performing a reaction under a nitrogen stream at 100° C. for 3 hours, and 500 g of a reaction product having a rate of esterification of 88% was obtained.

Example 12

107.0 g (0.232 mol) of hexaglycerol and 394.8 g (1.390 mol) of stearic acid were put into a reaction container, and 0.25 g of sodium hydroxide was added thereto, reaction under a nitrogen stream at 240° C. for 7 hours, and 477 g of an esterification reaction product was obtained. 477 g of the aforementioned ester and 27.3 g (0.232 mol) of succinic acid were put in a chamber for performing a reaction under a nitrogen stream at 100° C. for 3 hours, and 500 g of a reaction product having a rate of esterification of 88% was obtained.

Example 13

107.6 g (0.233 mol) of hexaglycerol and 394.2 g (1.398 mol) of oleic acid were put into a reaction container, and 0.25 g of sodium hydroxide was added thereto, to preform a reaction under a nitrogen stream at 240° C. for 7 hours, and 477 g of an esterification reaction product was obtained. 477 g of the aforementioned ester and 27.5 g (0.233 mol) of succinic acid were put in a chamber for performing a reaction under a nitrogen stream at 100° C. for 3 hours, and 500 g of a reaction product having a rate of esterification of 88% was obtained.

Example 14

92.6 g (0.200 mol) of hexaglycerol and 409.0 g (1.203 mol) of behenic acid were put into a reaction container, and 0.25 g of sodium hydroxide was added thereto, for performing a reaction under a nitrogen stream at 240° C. for 7 hours, and 480 g of an esterification reaction product was obtained. 480 g of the aforementioned ester and 23.7 g (0.200 mol) of succinic acid were put in a chamber for performing a reaction under a nitrogen stream at 100° C. for 3 hours, and 500 g of a reaction product having a rate of esterification of 88% was obtained.

Example 15

101.9 g (0.220 mol) of hexaglycerol and 375.7 g (1.323 mol) of isostearic acid were put into a reaction container, and 0.25 g of sodium hydroxide was added thereto, for performing a reaction under a nitrogen stream at 240° C. for 7 hours, and 454 g of an esterification reaction product was obtained. 454 g of the aforementioned ester and 50.3 g (0.220 mol) of octenylsuccinic acid were put in a chamber for performing a reaction under a nitrogen stream at 100° C. for 3 hours, and 500 g of a reaction product having a rate of esterification of 88% was obtained.

Example 16

105.7 g (0.229 mol) of hexaglycerol and 389.8 g (1.372 mol) of isostearic acid were put into a reaction container, and 0.25 g of sodium hydroxide was added thereto, for performing a reaction under a nitrogen stream at 240° C. for 7 hours, and 471 g of an esterification reaction product was obtained. 471 g of the aforementioned ester and 33.4 g (0.229 mol) of adipic acid were put in a chamber for performing a reaction under a nitrogen stream at 240° C. for 5 hours, and 500 g of a reaction product having a rate of esterification of 88% was obtained.

Comparative Example 1

99.4 g (0.215 mol) of hexaglycerol and 427.7 g (1.506 mol) of isostearic acid were put into a reaction container, and 0.25 g of sodium hydroxide was added thereto, for performing a reaction under a nitrogen stream at 240° C. for 7 hours, and 500 g of a reaction product having a rate of esterification of 88% was obtained.

Comparative Example 2

198.8 g (0.43 mol) of hexaglycerol and 355.4 g (3.012 mol) of succinic acid were put into a reaction container, and 0.25 g of sodium hydroxide was added thereto, to perform a reaction under a nitrogen stream at 100° C. for 5 hours, and 500 g of a reaction product having a rate of esterification of 88% was obtained.

Powder Dispersion Composition

Examples 17 to 32

5.0 g of the esterification reaction product obtained in each of Examples 1 to 16, 45.0 g of isotridecyl isononanoate, and 50.0 g of titanium oxide fine particles (aluminum hydroxide, stearic acid treated product) were dispersed using a bead mill, and titanium oxide dispersion compositions of Examples 17 to 32 were obtained.

Comparative Example 3 and 4

Using the esterification reaction products obtained in Comparative Examples 1 and 2 instead of those obtained in Examples 1 to 16, the dispersion was performed in the same manner, and titanium oxide dispersion compositions of Comparative Examples 3 and 4 were obtained.

Examples 33 to 36

5.0 g of the esterification reaction product obtained in each of Examples 4, 10, 13, and 15, 35.0 g of isotridecyl isononanoate, and 60.0 g of zinc oxide fine particles (silicone treated product) were dispersed in the same manner, zinc oxide dispersion compositions of Examples 33 to 36 were obtained.

Comparative Examples 5 and 6

Using the esterification reaction products obtained in Comparative Examples 1 and 2, the dispersion was performed in the same manner, and zinc oxide dispersion compositions of Comparative Examples 5 and 6 were obtained.

Examples 37 to 39

5.0 g of the esterification reaction product obtained in Example 4, 45.0 g of an oil agent, and 50.0 g of titanium oxide fine particles (aluminum hydroxide, stearic acid treated product) were dispersed using a bead mill, titanium oxide dispersion compositions of Examples 37 to 39 were obtained.

The dispersibility of the powder dispersion compositions obtained as above was observed by a microscope to evaluate the degree of aggregation. The results are shown in Tables 1-4. Hereinafter, evaluations of the Examples and the Comparative Examples are explained any one of "Excellent (shown as "⊚" in the tables)", "Good (shown as "○" in the tables)", "Fair (shown as "Δ" in the tables)", and "Poor (shown as "x" in the tables)" as their evaluation indexes. The Examples of the invention have any one of "Excellent", "Good" or "Fair" evaluation, while the Compatible Examples have "Poor" evaluation.
(Evaluation Criteria)
Excellent: No aggregation observed
Good: Slight aggregation observed
Fair: A little aggregation observed
Poor: Aggregation observed The stability over time when the powder dispersion compositions obtained as above were allowed to stand still at 25° C. for one day was observed by a microscope to evaluate the degree of aggregation. The results are shown in Tables 1-4.
(Evaluation Criteria)
Excellent: No aggregation observed
Good: Slight aggregation observed
Fair: A little aggregation observed
Poor: Aggregation observed The stickiness of the powder dispersion compositions obtained as above was evaluated by 10 panelists. The results are shown in Tables 1-4.
(Evaluation Criteria)
Excellent: 9 or more out of 10 people answered "Non-sticky".
Good: 7 or more out of 10 people answered "Non-sticky".
Fair: 5 or more out of 10 people answered "Non-sticky".
Poor: 4 or less out of 10 people answered "Non-sticky".

TABLE 1

|  | Example | | | | | | | | |
| --- | --- | --- | --- | --- | --- | --- | --- | --- | --- |
|  | 17 | 18 | 19 | 20 | 21 | 22 | 23 | 24 | 25 |
| Reaction Product (Example) | 1 | 2 | 3 | 4 | 5 | 6 | 7 | 8 | 9 |
| Molar ratio * | 86/14 | 86/14 | 86/14 | 86/14 | 86/14 | 50/50 | 75/25 | 95/5 | 86/14 |
| Dispersibility | ○ | ○ | ⊚ | ⊚ | ⊚ | ○ | ⊚ | ⊚ | ○ |
| Stability over time | ○ | ○ | ⊚ | ⊚ | ⊚ | ⊚ | ⊚ | ⊚ | ○ |
| Greasiness | ⊚ | ⊚ | ⊚ | ⊚ | ○ | ⊚ | ⊚ | ○ | ⊚ |

TABLE 2

|  | Example | | | | | | | Comparative Example | |
| --- | --- | --- | --- | --- | --- | --- | --- | --- | --- |
|  | 26 | 27 | 28 | 29 | 30 | 31 | 32 | 3 | 4 |
| Reaction Product (Example) | 10 | 11 | 12 | 13 | 14 | 15 | 16 | 1 | 2 |
| Molar ratio * | 86/14 | 86/14 | 86/14 | 86/14 | 86/14 | 86/14 | 86/14 | 100/0 | 0/100 |
| Dispersibility | ⊚ | ○ | ⊚ | ⊚ | ⊚ | ⊚ | ⊚ | X | X |
| Stability over time | ⊚ | ○ | ⊚ | ⊚ | ⊚ | ⊚ | ⊚ | X | X |
| Greasiness | ⊚ | ⊚ | Δ | ⊚ | Δ | ⊚ | ○ | ○ | ○ |

TABLE 3

|  | Example | | | | Comparative Example | |
| --- | --- | --- | --- | --- | --- | --- |
|  | 33 | 34 | 35 | 36 | 5 | 6 |
| Reaction Product (Example) | 4 | 10 | 13 | 15 | 1 | 2 |
| Molar ratio * | 86/14 | 86/14 | 86/14 | 86/14 | 100/0 | 0/100 |
| Dispersibility | ◎ | ◎ | ◎ | ◎ | X | X |
| Stability over time | ◎ | ◎ | ◎ | ◎ | X | X |
| Greasiness | ◎ | ◎ | ◎ | ◎ | ○ | ○ |

* Mixing molar ratio of monovalent carboxylic acid to divalent carboxylic acid

TABLE 4

|  | Example | | |
| --- | --- | --- | --- |
|  | 37 | 38 | 39 |
| Reaction Product (Example) | 4 | 4 | 4 |
| Molar ratio * | 86/14 | 86/14 | 86/14 |
| Oil agent | Liquid paraffin | Decamethylcyclo-pentasiloxane | Glycery tri (caprylate/caprate) |
| Dispersibility | ◎ | ◎ | ◎ |
| Stability over time | ◎ | ◎ | ◎ |
| Greasiness | ◎ | ◎ | ◎ |

* Mixing molar ratio of monovalent carboxylic acid to divalent carboxylic acid

As shown in Tables 1-4, the powder dispersion compositions of Examples 17 to 39 using the powder dispersants of Examples 1 to 16 had excellent dispersibility and excellent stability over time with no stickiness. In contrast, the powder dispersion compositions of Comparative Examples 3 to 6 using Comparative Examples 1 to 2 had a low dispersibility.

Example 40 (Sunscreen Water-in-Oil (W/O) Milky Lotion)

(Compounds) (wt %)
1. Glyceryl tri(caprylate/caprate): 4.0
2. Decamethylcyclopentasiloxane: 14.0
3. Crosslinked polyether modified silicone crosslinked product (Note 1): 3.0
4. Alkyl-polyether co-modified silicone (Note 2): 1.5
5. Titanium oxide dispersion composition (Example 20): 25.0
6. Zinc oxide dispersion composition (Example 33): 35.0
7. Pentylene glycol: 1.0
8. 1,3-Butylene glycol: 3.0
9. Sodium citrate: 0.2
10. Magnesium sulfate: 0.5
11. Preservative: appropriate quantity (less than 1 wt %)
12. purified water: Balance
(Note 1) Crosslinked polyether modified silicone crosslinked product: KSG-240 (manufactured by Shin-Etsu Chemical Co., Ltd.)
(Note 2) Alkyl-polyether co-modified silicone: KF-6038 (manufactured by Shin-Etsu Chemical Co., Ltd.)
(Production Method)
A: Uniformly mixing compounds 7 to 12.
B: Making compounds 1 to 4 uniform, and adding A, and emulsifying.
C: Adding compounds 5 and 6 to B, and mixing them to obtain sunscreen W/O milky lotion.

Example 40 according to the exemplary embodiment was a sunscreen W/O milky lotion having usability without powder aggregation, with excellent dispersion stability, and further with good spreadability to the skin, with smoothness without stickiness, with a high transparency, without powdery finish, and with excellent cosmetic durability.

Example 41 (Sunscreen W/O Milky Lotion)

(Compounds) (wt %)
1. Decamethylcyclopentasiloxane: 15.0
2. Neopentyl glycol dicaprate: 8.0
3. Ethylhexyl methoxycinnamate: 6.0
4. Diethylamino hydroxybenzoyl hexyl benzoate: 1.0
5. Alkyl-polyether co-modified silicone (Note 3): 1.5
6. Titanium oxide dispersion composition (Example 23): 10.0
7. Zinc oxide dispersion composition (Example 34): 20.0
8. 1,3-Butylene glycol: 4.0
9. Preservative: appropriate quantity
10. Purified water: Balance
(Note 3) Alkyl-polyether co-modified silicone: ES-5300 (manufactured by Dow Corning Toray Co., Ltd.)
(Production Method)
A: Uniformly mixing compounds 8 to 10.
B: Heating compounds 1 to 5 to make them uniform, followed by addition of A, to perform emulsification.
C: Adding compounds 6 and 7 to B, followed by mixing, to obtain sunscreen W/O milky lotion.

Example 41 according to the exemplary embodiment was a sunscreen W/O milky lotion having usability without powder aggregation, with excellent dispersion stability, and further with good spreadability to the skin, with smoothness without stickiness, with a high transparency, without powdery finish, and with excellent cosmetic durability.

Example 42 (Sunscreen W/O Cream)

(Compounds) (wt %)
1. Polyglyceryl-2 isostearate (Note 4): 1.2
2. Polyglyceryl-6 polyricinoleate (Note 5): 0.2
3. Polyglyceryl-10 laurate (Note 6): 0.15
4. Macadamia nut oil polyglyceryl-6 estersbehenate (Note 7): 1.0
5. Isododecane: 10.45
6. Titanium oxide dispersion composition (Example 29): 20.0
7. Ethylhexyl methoxycinnamate: 7.5
8. Diethylamino hydroxybenzoyl hexyl benzoate: 2.5
9. Disteardimonium hectorite: 1.0
10. 1,3-Butylene glycol: 10.0
11. Sodium chloride: 0.5
12. Preservative: appropriate quantity
13. Purified water: Balance
(Note 4) S Face IS-201P, manufactured by SAKAMOTO YAKUHIN KOGYO CO., LTD.
(Note 5) S Face CR-1001, manufactured by SAKAMOTO YAKUHIN KOGYO CO., LTD.
(Note 6) S Face L-1001, manufactured by SAKAMOTO YAKUHIN KOGYO CO., LTD.
(Note 7) S Face VL-211, manufactured by SAKAMOTO YAKUHIN KOGYO CO., LTD.
(Production Method)
A: Heating compounds 1 to 9 to make them uniform.
B: Heating compounds 10 to 13 to make them uniform.

C: Adding B to A to perform emulsification, followed by cooling, to obtain sunscreen W/O cream.

Example 42 according to the exemplary embodiment was a sunscreen W/O cream having usability without powder aggregation, with excellent dispersion stability, and further with good spreadability to the skin, with smoothness without stickiness, with a high transparency, without powdery finish, and with excellent cosmetic durability.

Example 43 (Sunscreen Oil-in Water (O/W) Cream)

(Compounds) (wt %)
1. Glyceryl tri(caprylate/caprate): 5.0
2. Titanium oxide dispersion composition (Example 31): 25.0
3. Zinc oxide dispersion composition (Example 35): 20.0
4. (Hydroxyethyl acrylate/sodium acryloyldimethyltaurate) copolymer (Note 8): 1.0
5. Sorbitan stearate: 1.5
6. Isostearic acid PEG-60 glyceryl: 1.5
7. Coconut oil fatty acid sucrose: 0.5
8. 1,3-butylene glycol: 8.0
9. Glycerol: 4.0
10. 2 wt % Xanthan gum: 2.0
11. Preservative: appropriate quantity
12. Purified water: Balance
(Note 8) (Hydroxyethyl acrylate/sodium acryloyldimethyltaurate) copolymer: Simulgel NS (manufactured by SEPPIC Inc.)
(Production Method)
A: Mixing compounds 1 to 3, followed by heating.
B: Heating compounds 4 to 12 to make them uniform.
C: Adding A to B to perform emulsification, followed by cooling, to obtain sunscreen O/W cream.

Example 43 according to the exemplary embodiment was a sunscreen O/W cream having usability without powder aggregation, with excellent dispersion stability, and further with good spreadability to the skin, with smoothness without stickiness, with a high transparency, without powdery finish, and with excellent cosmetic durability.

Example 44 (W/O Cream Foundation)

(Compounds) (wt %)
1. Polyglyceryl-2 isostearate (Note 4): 1.2
2. Polyglyceryl-6 polyricinoleate (Note 5): 0.2
3. Polyglyceryl-10 laurate (Note 6): 0.15
4. Macadamia nut oil polyglyceryl-6 estersbehenate (Note 7): 1.0
5. Cyclopentasiloxane: 10.55
6. Isotridecyl isononanoate: 5.0
7. Distearidmonium hectorite: 1.0
8. Powder dispersant (Example 4): 0.4
9. Isotridecyl isononanoate: 4.0
10. Pigment (silicone treated): 8.5
11. Diglycerol (Note 9): 3.0
12. 1,3-Butylene glycol: 10.0
13. Preservative: appropriate quantity
14. Perfume: appropriate quantity
15. Purified water: Balance
(Note 9) Diglycerol 801, manufactured by SAKAMOTO YAKUHIN KOGYO CO., LTD.
(Production Method)
A: Heating compounds 1 to 7 to make them uniform.
B: Mixing compounds 8 to 10 to uniformly disperse them.
C: Adding A to B to be dispersed.
D: Heating compounds 11 to 15 to be uniformly mixed.
E: Gradually adding D to C under stirring to perform emulsification, followed by cooling, to obtain W/O cream foundation.

Example 44 according to the exemplary embodiment was an W/O cream foundation having excellent dispersion stability and fine texture without aggregation of powder, further having good spreadability to the skin and smoothness without stickiness or oiliness, giving moist, fresh, and refreshed feeling of use, and having good cosmetic retention and excellent stability without changes due to temperature or time.

INDUSTRIAL APPLICABILITY

A cosmetic product having good spreadability with less stickiness can be provided by mixing the powder dispersant and the powder dispersion composition of the exemplary embodiment in the cosmetic product. The powder dispersant of the exemplary embodiment can be used for a wide range of applications such as skin cosmetics including facial foam/cream, cleansing, massage cream, pack, lotion, milky lotion, cream, serum, makeup base, and sunscreen, and finishing cosmetics including foundation, white powder, eye shadow, eyeliner, mascara, eyebrow, concealer, lipstick, lip gloss, and lip balm.

What is claimed is:
1. A powder dispersion composition, comprising;
(a) an ester compound that is a two-stage esterification reaction product of:
a polyglycerol having an average degree of polymerization of the polyglycerol, calculated from its hydroxyl value, ranging from 2 to 20,
a monovalent carboxylic acid or at least one derivative thereof, and
a divalent carboxylic acid or at least one derivative thereof, and that has a rate of esterification that is equal to or greater than 75% and an acid value that ranges from 22.5 to 112.7 due to a two-stage esterification reaction including reacting to esterify the monovalent carboxylic acid or the at least one derivative thereof and the polyglycerol to obtain an initial esterification reaction product followed by reacting to esterify the divalent carboxylic acid or the at least one derivative thereof and the initial esterification reaction product to obtain said ester compound;
(b) an oil agent; and
(c) at least one powder selected from the group consisting of an inorganic powder, a luminescent powder, an organic powder, a dye powder, a metal powder and a composite powder.

2. A cosmetic product comprising the powder dispersion composition according to claim 1.

3. A method of providing a powder dispersion, comprising dissolving or dispersing the powder dispersant according to claim 1 in at least one oil agent.

4. A powder dispersion composition, comprising;
(a) an ester compound that is a two-stage esterification reaction product of:
a polyglycerol having an average degree of polymerization of the polyglycerol, calculated from its hydroxyl value, ranging from 2 to 20,
a monovalent carboxylic acid or at least one derivative thereof, the monovalent carboxylic acid being selected from the group consisting of a 2-ethylhexanoic acid, an isononanoic acid, an isomyristic acid, an isopalmitic acid, an isostearic acid, a ricinoleic acid, an oleic acid, a linoleic acid, a linolenic acid, an isoarachidic acid and an erucic acid and acid halides thereof, and a divalent carboxylic acid or at least one derivative thereof, and that has a rate of esterification that is equal to or greater than 75% and an acid value that ranges from 22.5 to 112.7 due to a two-stage esterification reaction including reacting to esterify the monovalent carboxylic acid or the at least one derivative thereof and the polyglycerol to obtain an initial esterification reaction product followed by reacting to esterify the divalent carboxylic acid or the at least one derivative thereof and the initial esterification reaction product to obtain said ester compound;

(b) an oil agent; and (c) at least one powder selected from the group consisting of an inorganic powder, a luminescent powder, an organic powder, a dye powder, a metal powder, and a composite powder.

5. A cosmetic product comprising the powder dispersion composition according to claim 4.

6. A method of providing a powder dispersion, comprising:

dissolving or dispersing the powder dispersant according to claim 4 in at least one oil agent.

7. The powder dispersion composition to claim 1, wherein the monovalent carboxylic acid in the ester compound is selected from the group consisting of a 2-ethylhexanoic acid, an isononanonic acid, an isomyristic acid, an isopalmitic acid, an isostearic acid, a ricinoleic acid, an oleic acid, a linoleic acid, a linolenic acid, an isoarachidic acid, an erucic acid, and an acid halide thereof.

8. The powder dispersion composition to claim 1, wherein the divalent carboxylic acid in the ester compound is selected from the group consisting of oxalic acid, malonic acid, succinic acid, glutaric acid, adipic acid, pimelic acid, suberic acid, azelaic acid, sebacic acid, dimethyloctadecanedioic acid, eicosanedioic acid, phtalic acid, isophtalic acid, terephtalic acid, maleic acid, dimer acid, tetrahydrophtalic acid, octenylsuccinic acid, and dodecenylsuccinic acid, an acid anhydride, and an acid halide thereof.

9. The powder dispersion composition to claim 4, wherein the divalent carboxylic acid in the ester compound is selected from the group consisting of oxalic acid, malonic acid, succinic acid, glutaric acid, adipic acid, pimelic acid, suberic acid, azelaic acid, sebacic acid, dimethyloctadecanedioic acid, eicosanedioic acid, phtalic acid, isophtalic acid, terephtalic acid, maleic acid, dimer acid, tetrahydrophtalic acid, octenylsuccinic acid, and dodecenylsuccinic acid, an acid anhydride, and an acid halide thereof.

* * * * *